United States Patent [19]

Sashin et al.

[11] Patent Number: 4,946,238
[45] Date of Patent: Aug. 7, 1990

[54] FIBER OPTIC COUPLER

[75] Inventors: Donald Sashin, Pittsburgh, Pa.; Ernest J. Sternglass, Bloomington, Ind.

[73] Assignee: University of Pittsburgh, Pittsburgh, Pa.

[21] Appl. No.: 332,589

[22] Filed: Apr. 3, 1989

Related U.S. Application Data

[60] Continuation of Ser. No. 220,054, Jul. 15, 1988, abandoned, which is a continuation of Ser. No. 832,429, Feb. 24, 1986, abandoned, which is a division of Ser. No. 574,588, Jan. 27, 1984, Pat. No. 4,696,022.

[51] Int. Cl.$^5$ .............................................. G02B 6/08
[52] U.S. Cl. ................................ 350/96.27; 358/111; 358/901; 378/41; 378/99
[58] Field of Search ............... 350/96.24, 96.25, 96.27; 358/901, 111; 378/41, 42, 99

[56] References Cited

U.S. PATENT DOCUMENTS

| | | | |
|---|---|---|---|
| 3,043,910 | 7/1962 | Hicks, Jr. | 350/96.27 |
| 3,058,021 | 10/1962 | Dunn | 358/111 |
| 3,432,657 | 3/1969 | Slavin | 378/41 |
| 3,767,931 | 10/1973 | Williams | 378/153 |
| 3,796,905 | 3/1974 | Tomii et al. | 350/96.27 X |
| 3,829,701 | 8/1974 | Hura | 378/153 |
| 3,866,047 | 2/1975 | Hounsfield | 378/18 |
| 3,934,151 | 1/1976 | Stowe et al. | 378/160 |
| 3,947,689 | 3/1976 | Wagner | 378/151 |
| 3,973,127 | 8/1976 | Matsuda et al. | 378/24 |
| 4,010,371 | 3/1977 | LeMay | 250/366 |
| 4,029,964 | 6/1977 | Ashe | 250/368 |
| 4,090,104 | 5/1978 | Vann et al. | 350/96.27 X |
| 4,139,261 | 2/1979 | Hilsum | 350/96.27 |
| 4,149,082 | 4/1979 | Haendle et al. | 378/22 |
| 4,179,100 | 12/1979 | Sashin et al. | 250/370.09 |
| 4,214,267 | 7/1980 | Roese et al. | 358/111 |
| 4,344,668 | 8/1982 | Gunther et al. | 350/96.27 |
| 4,696,022 | 9/1987 | Sashin et al. | 378/41 |

OTHER PUBLICATIONS

E. E. Christensen et al., *An Introduction to the Physics of Diagnostic Radiology*, Ch. 19, (Lea & Febiger, Phila., 1978), pp. 268-278.

Kuroda et al., *Electromedia*, "The Clinical Value of Sequential Steroscopic Imaging with Cardoskop U", (No. 1, pp. 22-27, 1982).

Stauffer et al., "Progress in Stereofluoroscopy, 'Transmission': T-V Anaglyph Display and Color Cinerecording", *Radiology*, 82, pp. 125-126, (Jan. 1964).

Stauffer et al., "Stereoscopic Televised Fluroscopy", *Radiology*, 79, pp. 30-34, (Jul. 1962).

Snow, "Self-Scanning Photodiode Arrays for Spectroscopy", *Research Development*, Apr. 1976, pp. 18-22.

Nicoll, "Mural Television Display Using Fiber Optics", RCA TN No. 188, Sep. 1958, (1 page).

*Primary Examiner*—John D. Lee
*Attorney, Agent, or Firm*—Arnold B. Silverman; David V. Radack

[57] ABSTRACT

A fiber optic coupler connecting a scintillator which receives the X-ray energy and converts the X-ray energy into visible light photons and a self-scanning photodiode array which converts the visible light photons into electrical signals, the self-scanning photodiode array being smaller in length than the scintillator means. The fiber optic coupler comprises a light receiving end wall adjacent to the scintillator, a light discharging end wall adjacent to the self-scanning photodiode array, a pair of substantially parallel sidewalls that are oriented generally perpendicular to the light discharging end wall, an array of optic fibers oriented generally perpendicularly to the light discharging end wall and extending from the light receiving end wall to the light discharging end wall. The light receiving end wall is greater in length than the light discharging end wall and at least some of the fibers in the array are different in length from other fibers in the array. Therefore, light entering the light receiving end wall is transported efficiently to the light discharging end wall and the image introduced into the fibers in the array at the light receiving end wall will be reduced as it passes through the fibers in the array in order that the self-scanning photodiode array means can be smaller in length than the scintillator.

3 Claims, 4 Drawing Sheets

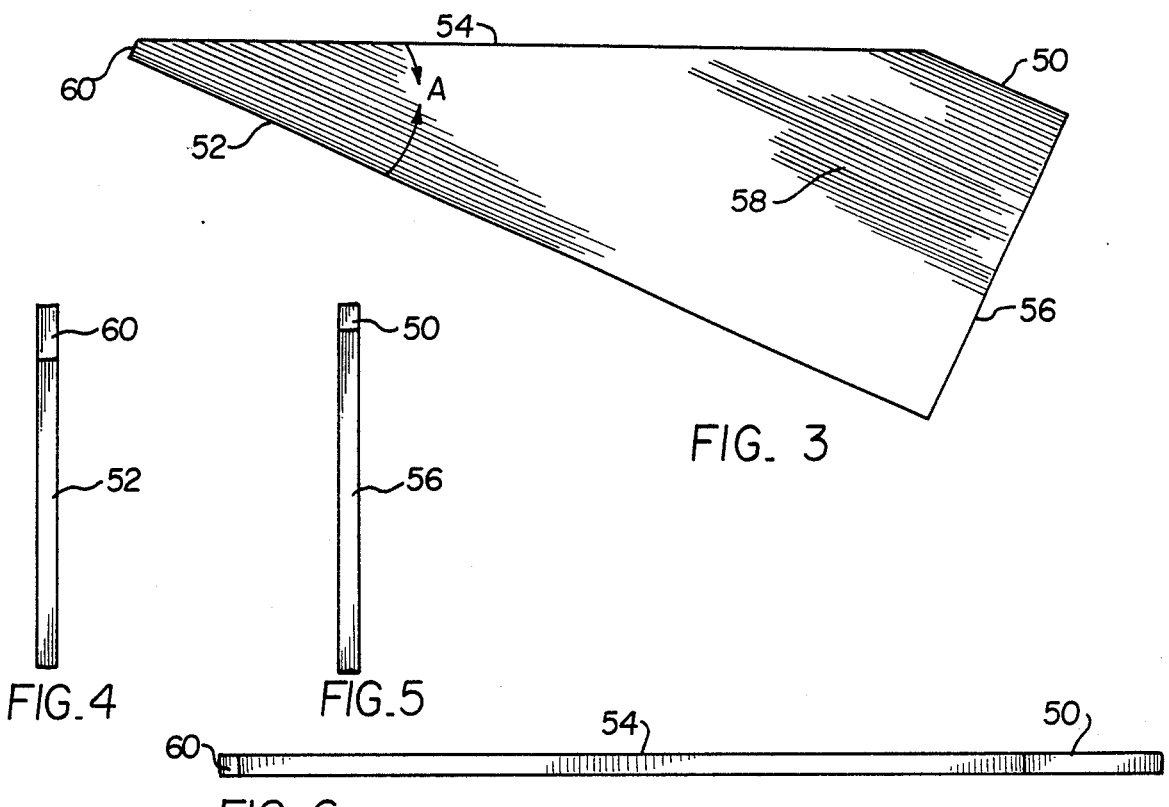
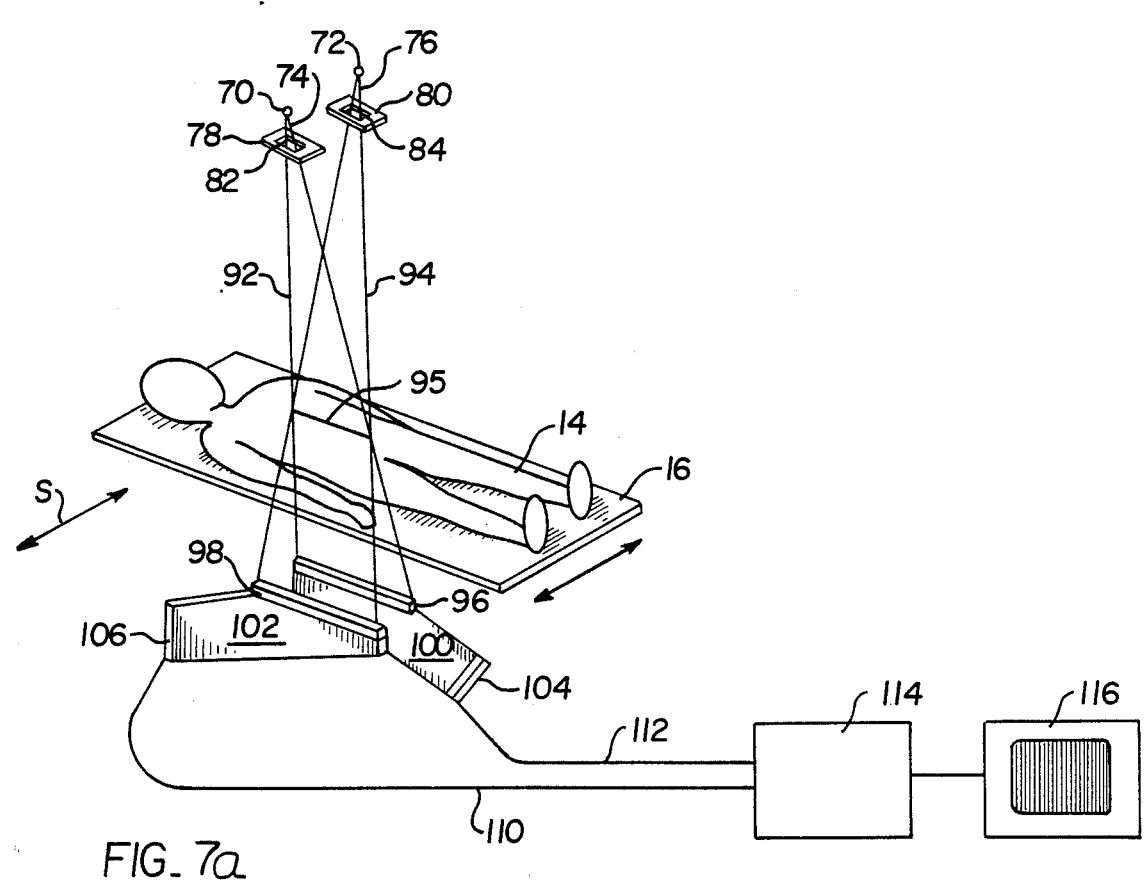

4,946,238

FIBER OPTIC COUPLER

This is a continuation of application Ser. No. 220,054, filed 7/15/88, now abandoned, which is a continuation of Ser. No. 832,429, filed 2/14/86, now abandoned, which is a division of Ser. No. 574,588, filed 1/27/84, now U.S. Pat. No. 4,696,022.

BACKGROUND OF THE INVENTION

1. Field of the Invention

This invention relates to stereoscopic radiography apparatus and an associated method and, more specifically, it relates to an efficient system for rapidly obtaining high resolution images even when the object being imaged is moving.

2. Description of the Prior Art

The advantageous use of radiation, such as x-rays, gamma rays and nuclear particles has long been known in medical, industrial and other environments A wide variety of systems and procedures have been employed in such uses depending, in part, upon safety considerations, the nature of the object to be imaged and equipment limitations. See generally U.S. Pat. Nos. 3,767,931; 3,829,701; 3,866,047; 3,934,151; 3,947,689 and 3,973,127. various forms of photodetectors, such as photomultipliers have been known in such systems. See generally U.S. Pat. Nos. 4,010,371 and 4,029,964. It has also been known to use self-scanning photodiode arrays for spectroscopy (Snow, Research-Development, April 1976) and for medical and non-medical units (see U.S. Pat. No. 4,179,100 the disclosure of which is hereby expressly incorporated herein by reference).

It has also been known to provide systems wherein collimated radiation is permitted to pass through an object and impinge upon a scintillator screen with fiber optic coupling means transporting the light to one or more arrays of self scanning photodiodes which emit a responsive electrical signal which may then be computer enhanced or otherwise processed or imaged. See U.S. Pat. No. 4,179,100.

Various suggestions regarding stereoscopic imaging used in connection with x-ray radiation have been made, but none has been provided which permits very rapid imaging so as to be adapted to be effective with rapidly moving members. See generally, An Introduction to the Physics of Diagnostic Radiology,, by E. E. Christensen et al chapter 19, (Lea and Febiger, Philadelphia, 1978); Kuroda et al., *Electromedica* (no. 1, pp. 22–27, 1/82; Stauffer et al., *Radiology*, 82 pp. 125–126 (1964); and Stauffer et al., *Radiology*, 79, pp. 30–34 (1962).

In spite of these prior disclosures, there remains a need for an effective means for high speed stereoscopic radiographic imaging.

SUMMARY OF THE INVENTION

The apparatus of the present invention in a preferred embodiment has met the above-described need by providing stereoscopic radiography apparatus employing two radiation beams which eminate from radiation source means and after collimation to achieve generally fan shaped beams are passed through an object. Radiation detector means receive radiation which has passed through the object being visualized and convert the radiation into responsive electrical signals. A form of detector means includes scintillator means which are optically coupled to a self-scanning array of photodiodes by fiber optic coupling means. Signal receiving means are operatively associated with the at least one array of photodiodes to store, process or display the image information.

In one embodiment, the beams are rapidly alternated with the radiation passing through the object being received by same scintillator means and the same photodiode means. In another embodiment, the beams are on simultaneously and are each received by separate scintillator means associated with separate arrays of photodiodes.

A unique fiber optic coupler is also provided. The fiber optic coupler has a pair of sidewalls, a light receiving end wall and a light discharging end wall. The light discharging end wall is preferably shorter and of lesser area than the light receiving end wall. The fibers are preferably of a number of different lengths. This permits a large area of radiation receipt to correspond to a small area of photodiode array.

It is an object of the present invention to provide stereoscopic radiography apparatus which is adapted to operate very rapidly.

It is a further object of the present invention to provide stereoscopic radiography apparatus and an associated method which will preserve image quality.

It is another object of the present invention to provide a stereoscopic radiography system which has high contrast sensitivity and high spatial resolution.

It is another object of the invention to provide stereoscopic radiography apparatus which is adapted for digital computer processing to enhance the image.

It is a further object of the present invention to provide such a system wherein a unique fiber optic coupler may advantageously be employed.

It is a further object of the invention to provide a system capable of obtaining two views of the same region of the object being studied substantially simultaneously.

These and other objects of the invention will be more fully understood from the following description of the invention on reference to the illustrations appended hereto.

BRIEF DESCRIPTION OF THE DRAWINGS

FIG. 3 is a front elevational view of a form of optic coupler of the present invention.

FIG. 4 is a right side elevational view of the optical coupler of FIG. 3.

FIG. 5 is a left side elevational view of the couple of FIG. 3.

FIG. 6 is a top plan view of the coupler of FIG. 3

FIG. 7(a) is a schematic illustration, partially exploded, of another embodiment of the invention.

DESCRIPTION OF THE PREFERRED EMBODIMENTS

As used herein, the term "object" or "test object" or words of similar import will refer to various types of objects through which it is desired to pass radiation for test or diagnostic purposes including, but not limited to, humans and animals, specimens removed from humans and animals, nondestructive testing and security purposes. While for purposes of clarity of description specific reference will be made herein to a preferred use in medical environments, it will be appreciated that other forms of objects may be employed in connection with the apparatus of this invention in addition to medical uses and such other uses are expressly contemplated.

As used herein, the terms "self-scanning array of photodiodes", "self-scanning integrated array of photodiodes" an words of similar import shall mean one or more integrated circuit elements having a plurality of photodiodes, each associated with a storage capacitor on which it integrates electrical charges and a multiplex switch for periodic readout by means of an integrated switch register scanning circuit. This term shall expressly include, but not be limited to, linear arrays having about 60 to 4096 (preferably about 256 to 4096) photodiodes per integrated circuit and the associated circuitry, as well as planar or rectangular arrays of photodiodes. These arrays may have about 70 photodiodes per linear millimeter of array, for example.

As used herein, the term "image information" shall refer to the electrical signals emerging from the photodiode array, images or data created by use of said electrical signals, with or without intervening storage or modification thereof and images created with or without addition to or subtraction from the image data.

As used herein in connection with a reference to a first radiation beam impinging on an object as related to the timing of a second radiation beam impinging upon the object, the term "substantially simultaneous" shall mean either having both beams concurrently operating or having the second beam turned on within less than about 10 milliseconds of turning off of the first beam.

Figure 1:
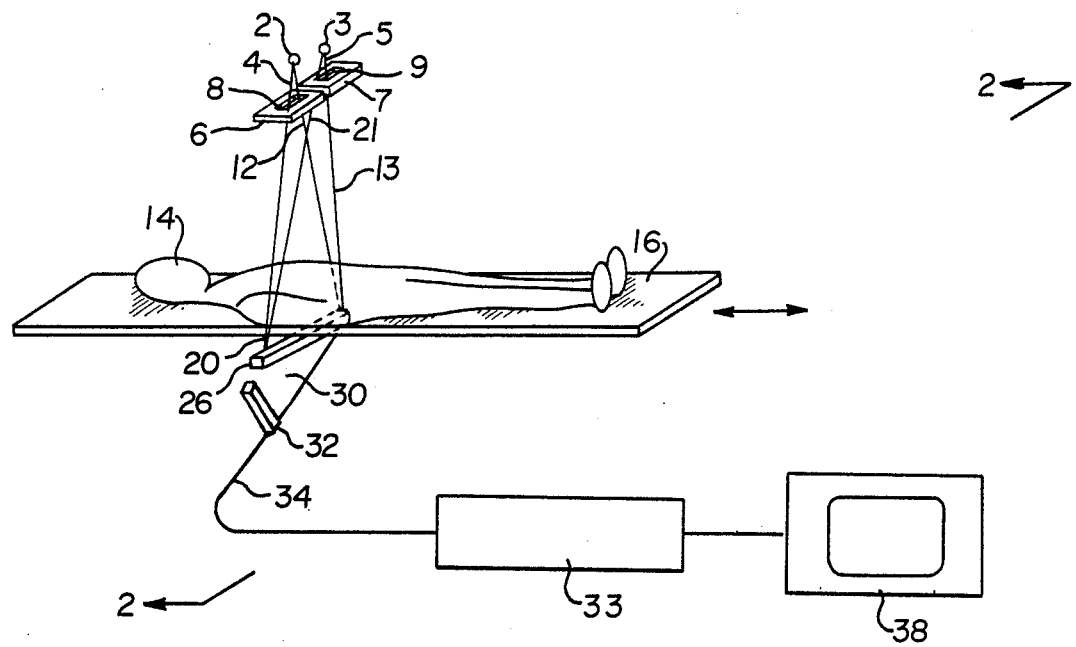
FIG. 1 is a schematic illustration of a form of stereoscopic radiography system of the present invention.
Figure 2:
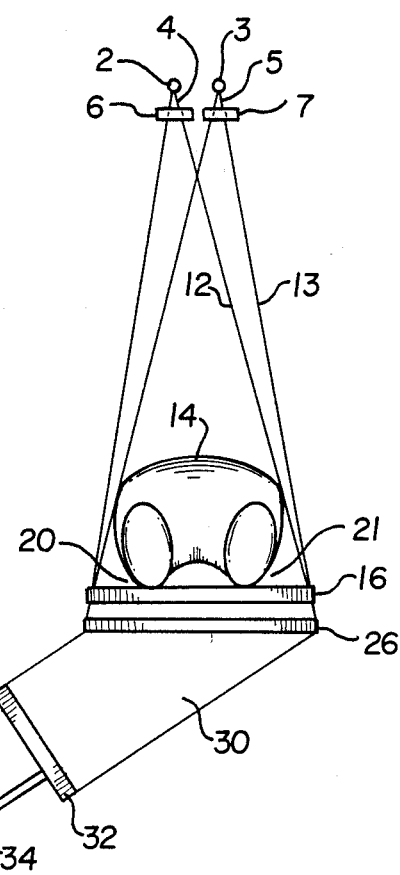
FIG. 2 is a cross-sectional illustration of the apparatus of FIG. 1 taken through 2—2.

Referring now more specifically to FIGS. 1 and 2 there is shown a pair of radiation sources 2, 3 which, in the form shown, are x-ray generators. It will be appreciated that other sources of radiation such as gamma-rays, for example, may be employed. These two sources 2, 3 may conveniently be separate x-ray tubes or a dual anode x-ray tube, for example. X-ray beams 4, 5 respectively, are emitted by radiation sources 2, 3. Collimators 6, 7 are positioned in the path of the beams, respectively, 4, 5. Each collimator 6, 7 has an associated slit 8, 9 which converts the generally conical x-ray beam 4, 5 into a generally flat fan shaped beam 12, 13.

In the form illustrated, the object to be subjected to the radiography is a patient 14 shown reclining on a moveable support table 16 which is adapted to be reciprocated in the directions indicated by the arrows. This movement of the support table 16 with respect to the rest of the radiography apparatus permits sequential exposure of various portions of the patient to the fan-shaped x-ray beams 12, 13. Alternatively, if desired, the patient can remain stationary and the rest of the apparatus may be moved relative to the patient in order to achieve the same objective. The portions of the beams 12, 13 which have passed through the patient 14 are indicated generally by the numbers 20 21.

Underlying the table 16 and receiving the radiation 20 21 from each beam 12, 13 passing through the patient 14 is the radiation detector which, in the form illustrated includes scintillator means 26 and self-scanning photodiode array 32. The scintillator means 26, which may be a relatively narrow phosphor screen, converts the x-ray energy into visible light photons. For certain systems, such as in cases where low KVP is employed and silicon or germanium diodes are used with low intensity radiation, the radiation may be allowed to impinge directly on the diodes without the use of separate scintillator means.

Also, if desired, fiber optic means which serve to deliver light emitted by the scintillator means may contain the scintillator means or the scintillator means could be in the form of closely packed fibers of fluorescing glass provided in bundles.

Positioned in face-to-face adjacency with the scintillator means 26 is the fiber optic coupler 30 which is adapted to transport light from the scintillator means to the self-scanning array of photodiodes 32. The self-scanning linear array of photodiodes 32 emits electrical signals which correspond to the light which impinges thereon. The electrical signals, which contain image information, are then delivered to the electrical processing unit 33 by means of electrical wire 34. In a preferred embodiment, the electrical processing unit 33 may consist of a digital computer which receives electrical signals in a memory bank and then, with or without modification thereof, presents the desired image in desired output form such as by presenting a visual image, a stored image or a computer printout of the data. In the form shown in FIG. 1, the image is presented on cathode-ray tube 38, but it may be displayed on any other suitable display means.

It is preferred that the x-ray sources 2, 3 be spaced from each other a distance equal to about 1 to 4 inches. It is noted that this embodiment places photodiodes 32 out of the path of the x-ray beam.

It has long been known that it is difficult to produce stereoscopic images where there is rapid motion, such as a rapidly moving heart or the flow of blood in vessels such as occurs in angiography of the coronary arteries. The present invention overcomes problems inherent in such needs by obtaining two stereoscopic images of rapidly moving or changing systems, either within a few milliseconds of each other or simultaneously while preserving image quality and allowing digital enhancement for improved visualization.

The apparatus shown in FIGS. 1 and 2 provides use of high detailed line-scanning of the image in such a way as to produce two separate substantially simultaneously generated stereoscopic views of the object as distinguished from two separate views scanned in their entirety in sequence. As each line can be scanned in a few milliseconds or less, motion is effectively frozen and maximum detail is obtained in the two stereoscopic images that are recorded line-by-line a few milliseconds apart.

In the embodiment shown in FIGS. 1 and 2, the two beams share the same detector systems and are, therefore, energized alternately. In operation, each x-ray source 2, 3 will be energized for about 2 to 4 milliseconds after which it will be turned off and the other source will immediately be energized for a like period. The single line of one of the two required images which is generated during the period when each source 2, 3 is on will then be digitally recorded using known amplifiers and analog-digital converters which form a portion of the electrical processing unit 33 along with the computer. This alternating process is repeated line-by-line until two complete sets of images are produced by way of the two x-ray sources.

The resultant recorded stereo image may then be viewed on a cathode-ray tube 38 or television monitor or other suitable means for examination in a number of possible ways. The view may be observed, for example, with electronically gated glasses which may be gated alternately employing crossed polarized glasses and a gated quarter-wave plate. Alternately, the image may be produced in two different colors such as red and green and may be viewed with suitably colored glasses wherein each lens will filter one color and permit the others to pass therethrough.

Referring to FIGS. 3 to 6, a preferred form of optical coupling means will be considered. The optical coupler has a pair of sidewalls 50, 52 which in the form shown are generally parallel to each other, a light receiving end wall 54 and a light discharging end wall 56. The individual fiber optic strands 58 are oriented generally parallel to the sidewalls 50, 52 and extend generally from end wall 54 to end wall 56. It will be appreciated that light received at end wall 54 will be transported by the fibers to end wall 56. In a typical installation the coupler may have a plurality of fiber strands each having a diameter of about 5 to 10 micrometers. It is noted that the coupler in the form shown is of substantially uniform thickness. The angle A between sidewall 52 and end wall 54 is preferably about 20 to 45 degrees.

Continuing to refer to FIGS. 3 through 6, it is note that as a result of the geometry of walls 50, 52, 54, 56 it will be appreciated that fibers of different lengths are provided in the optical coupler. If desired, the individual fibers may be tapered so as to converge toward wall 56.

In lieu of a plurality of individual fibers for optical coupling, one may employ a sheet of a suitable material (such as fiber glass, for example) having the desired properties.

As a result of the substantially uniform thickness of the optical coupler and the length of the light receiving end wall 54 being greater than the length of the light discharging end wall 56 it will be appreciated that the receiving end wall 54 may be substantially coextensive with the scintillator means and yet have the light received from the scintillator 26 efficiently delivered to a relatively smaller self-scanning array of light emitting photodiodes 32. This results in a reduction in cost of the diode array required to convert light impinging on wall 54 into a corresponding electrical signal. It is preferred that the end walls 54, 56 each be generally planar so as to facilitate efficient coupling with respectively a scintillator 26 and the photodiode array 32. For convenience of manufacture, a flat surface 60 is shown as being interposed between walls 52, 54, but this may be ignored in determining angle A and the other characteristics described hereinbefore.

An alternate to the optical coupler of FIGS. 3 through 6 would be to be employ the twisted or tapered fibers disclosed in our prior U.S. Pat. No. 4,179,100.

Referring to FIG. 7(a), an alternate embodiment of the invention which includes both x-ray generating systems being on at the same time and providing duplicate detection systems will now be considered. Radiation sources 70, 72 emit generally conical beams 74, 76, respectively, which are partially blocked by collimators 78, 80, respectively, which permit, through slots 82, 84 generally flat fan shaped beams 92, 94 to pass therethrough. While for clarity of illustration the radiation sources are shown as being spaced a substantial distance from each other, it is preferred that the spacing be about 1 to 4 inches. The patient 14 and support table 16 shown in FIG. 7(a) are subjected to relative movement to create a reciprocating scanning action in the direction indicated by double-headed arrow S. The portion of beams 92, 94 which pass through the object will be received, respectively, by scintillator means 96, 98. The radiation will be converted by the scintillator means 96, 98, such as a phosphor screen, into visible light which will be received, respectively, by fiber optic couplers 100, 102. While, for clarity of illustration the fiber optic couplers 100, 102 have been shown as being spaced from each other, it will generally be desirable to have them positioned sufficiently close to each other as to be recording generally the same sector of the object, while not receiving undesired levels of stray radiation from the adjacent beam. Preferably, there should be a space of about 1 to 4 inches between the two fiber optic couplers 100, 102. The light discharged by coupler 100 will be received in photodiode array 104 and the light discharged by coupler 102 will be received in photodiode array 106. The photodiode arrays 104, 106 will transfer image information by wires 110, 112 to the signal receiving means 114 wherein suitable amplifier means, analog-digital convertor means and digital computer means may be provided for storing, recording and, if desired, modifying the image data. The image data may be visualized on cathode-ray tube 116, if desired.

Figure 7B:
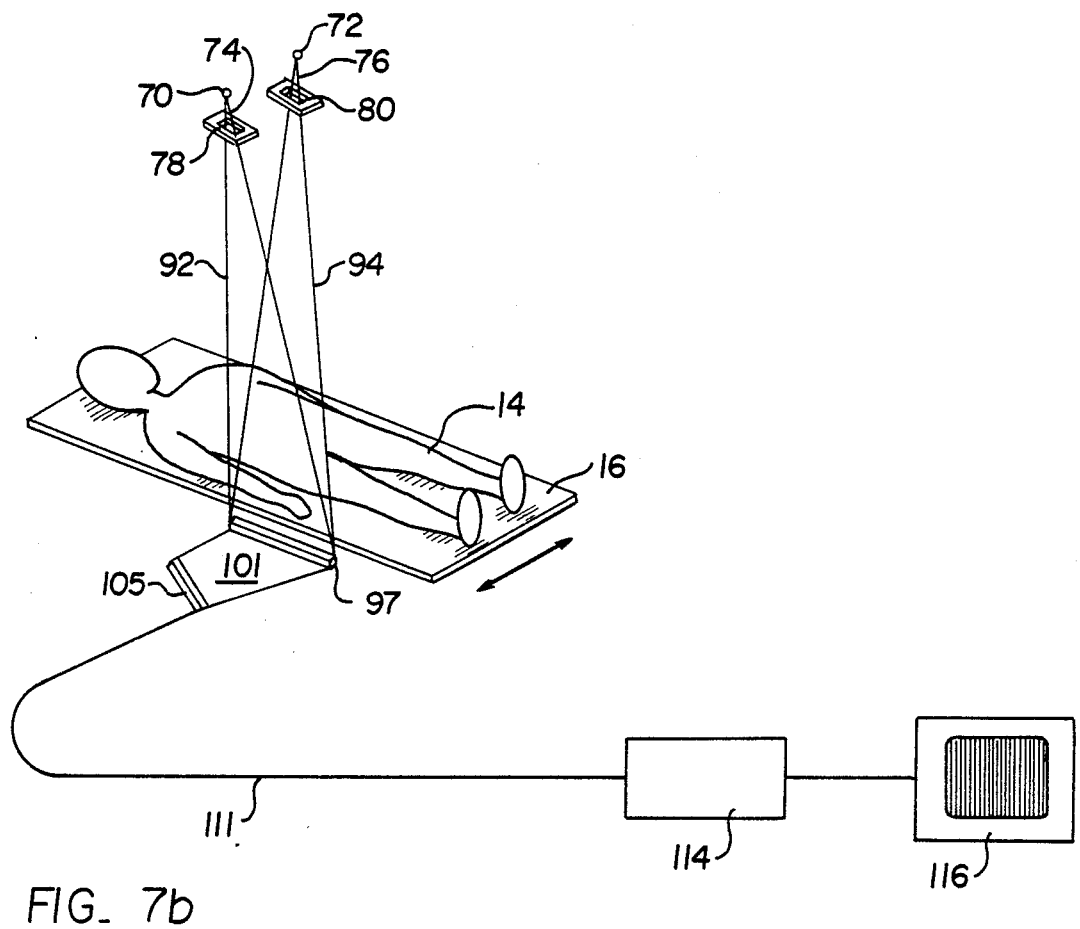
FIG. 7(b) is a schematic illustration of a further embodiment which is generally similar to FIG. 7(a).

FIG. 7(b) illustrates an embodiment similar to FIG. 7(a) except that as in the embodiment of FIGS. 1 and 2 a single detector system is employed and the two radiation beams are energized alternately. Scintillator means 97 alternately receives the portions of radiation beams 92, 94 which pass through patient 14 and converts the radiation to light which by fiber optic coupler 101 is delivered to diode array 105. The electrical signals emitted by diode array 105 is delivered by wire 111 to signal receiving means 114.

With this arrangement both x-ray generators 70, 72 may operate continuously and the individual images may be fed continuously to the signal receiving means 114. One of the advantages of this embodiment is that the heat loading efficiency of the x-ray tubes is improved so that more x-ray photons can be recorded and the image information quality thereby improved. One of the disadvantages of this embodiment is that the need to provide two independent detector systems increases the cost of the apparatus. As in the form shown in FIG. 7a, the two x-ray beams cross on a common line 95 within the patient, they both visualize the same part of the patient, but from a slightly different angle with both views being recorded substantially simultaneously.

Figure 8:
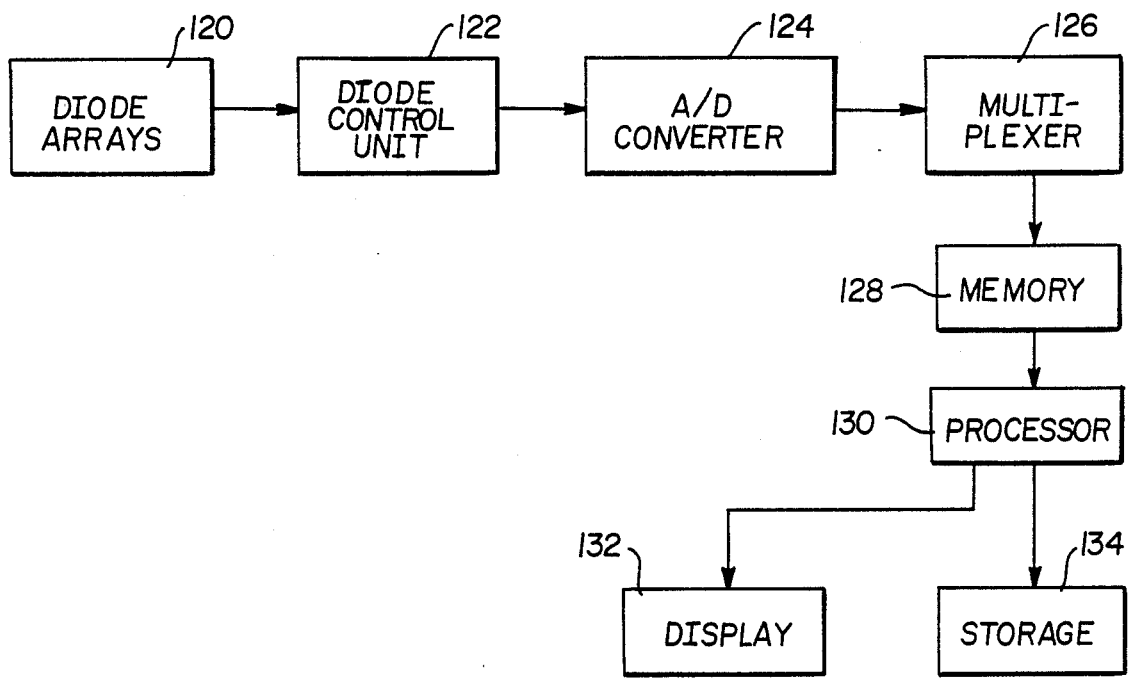
FIG. 8 is a block diagram of a form of data processing means of the present invention.

Referring to FIG. 8, a form of electrical processing means contemplated for use with the present invention will be considered. As the components and sequence of operations of these units are conventional and are well known to those skilled in the art a detailed explanation is not deemed necessary. The self-scanning photodiode arrays 120 detect the optical images from the scintillator by the optical coupler and convert the image into an electrical signal. The diodes are controlled by diode control unit 122 and the signal goes to the analog to digital converter 123 which converts the analog signal to a digital signal. The process is controlled by a multiplex circuit 126 and the digital pulses go to the computer memory 128 for storage. The stored signals are digitally processed in the processor 130 and may be displayed on display 132 and/or may be stored for future use with storage device 134, such as magnetic disks or tapes, digital tape, storage tubes, digital computer memory, video tape, photographs or electron beam tape recorders. Also, if desired, a camera may be employed to photograph the image appearing on display 132.

Figure 9:
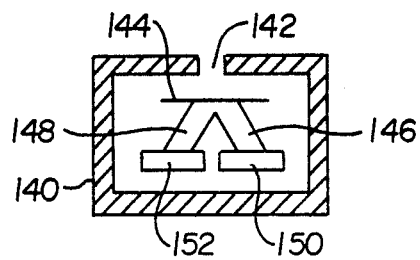
FIG. 9 is a cross-sectional illustration of a modified form of the self-scanning array of photodiodes and associated coupler.
Figure 10:
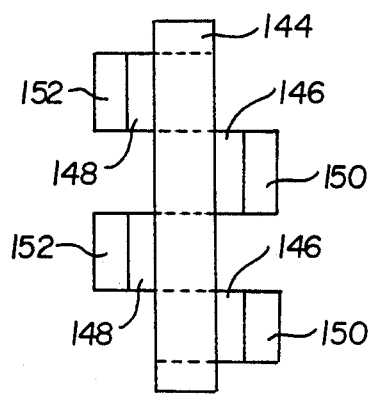
FIG. 10 is a top plan view of a portion of the photodiode array shown in FIG. 9.

Referring to FIGS. 9 and 10, a preferred form of a self-scanning photodiode array for use in the present invention will be considered. In this embodiment, an enclosure 140 which is light opaque is provided with an opening 142 into which the fan shaped beam of radiation which has passed through the object may pass. The scintillator 144 is in contact with a generally v-shaped fiber optic coupler which has a first series of legs 146 extending to one side and a second series of legs 148 extending to the other side. Associated with the fiber optic legs 146 are a series of self-scanning photodiode arrays 150. Associated with the fiber optic legs 148 are a series of self-scanning photodiode arrays 152. In operation, the x-ray will impinge upon the unitary scintillator strip 144 and will by the fiber optic means 146, 148 be delivered to the staggered arrays of self-scanning photodiodes 150, 152 with which the respective legs are associated. As is shown in FIG. 10, in this embodiment the self-scanning photodiode arrays 150, 152 are positioned in staggered fashion and are optically coupled to scintillator means 144 to provide continuous receipt of light emerging from the scintillator means by the arrays 150, 152. Alternate light pipes provide light to alternate photodiode arrays from alternate sections of the scintillator means 144. This embodiment provides unique means for minimizing the risk of undesired gaps in image information as displayed visually.

As an alternate to the preferred approach shown in FIGS. 9 and 10, precisely dimensioned self-scanning photodiode arrays may be placed in a linear close abutting relationship with direct fiber optic coupling so as to resist undesired gaps.

Figure 11:
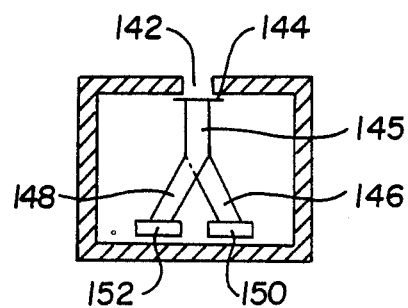
FIG. 11 is a cross-sectional illustration of a modified form of the staggered array shown in FIGS. 9 and 10.

FIG. 11 illustrates a modified form of staggered array which is generally similar to FIGS. 9 and 10 except that a series of alternating individual bent fiber optic couplers 145-152 or 145' (not shown)-150 deliver the light from the scintillator means 144, respectively, to photodiode array 152, 150.

It will be appreciated, therefore, that the present invention provides an effective means for obtaining rapid stereoscopic images in an efficient and economical fashion. By providing substantially simultaneous radiation exposure in a line-by-line fashion, movement of the portion of the object being subjected to radiography is arrested and high quality images are obtained. As the present invention facilitates use of narrow line detectors, most scattered radiation will miss the detector thereby preserving the image contrast without the need for Bucky grids.

While for purposes of illustration collimators with a single slit have been emphasized herein, it will be appreciated that if desired more than one slit in a given collimator or a single collimator having a slit for each beam may be provided if desired.

While specific reference has been made to a radiation source providing x-rays or gamma-rays, the invention is not so limited, and other forms of radiation such as particulate radiation including protons and mesons, for example, may be employed. In connection with particulate radiation as well as other forms, a generally rectangular beam having parallel sides may be used in lieu of a fan beam.

While for simplicity of disclosure reference has been made herein to the preferred use of self-scanning arrays of photodiodes as the preferred means of detecting radiation passing through the object being tested in stereoscopic imaging, it will be appreciated that the invention is not so limited. A general reference herein to "radiation detectors" shall be deemed to encompass these types of detectors. With respect to diode arrays, single linear arrays, multiple linear arrays, staggered arrays, arrays disposed generally in a single plane ("planar arrays") or other suitable patterns may be employed.

While for purposes of simplicity of description herein, in general, examples showing a vertically oriented radiation beam have been employed it will be appreciated that the radiation may be directed from any desired angle or angles and also the patient or object may be oriented or moved vertically or angularly with respect to the floor of the room.

Whereas particular embodiments of the invention have been described above for purposes of illustration, it will be evident to those skilled in the art that numerous variations of the details may be made without departing from the invention as defined in the appended claims.

We claim:
1. An apparatus converting X-ray energy to electrical signals comprising:
   a scintillator means which receives said X-ray energy and converts said X-ray energy into visible light photons;
   a self-scanning photodiode array means which converts said visible light photons into electrical signals, said self-scanning photodiode array means being smaller in length than said scintillator means; and
   a fiber optic coupler means connecting said scintillator means and said self-scanning photodiode array, said fiber optic coupler means comprising:
   a light receiving end wall adjacent to said scintillator means;
   a light discharging end wall adjacent to said self-scanning photodiode array means;
   a pair of substantially parallel sidewalls that are oriented generally perpendicular to said light discharging end wall;
   an array of optic fibers oriented generally perpendicularly to said light discharging end wall and extending from said light receiving end wall to said light discharging end wall;
   said light receiving end wall being of greater length than said light discharging end wall; and
   at least some of said fibers in said array being of different length from other fibers in said array, whereby light entering said light receiving end wall is transported efficiently to said light discharging end wall and the image introduced into said fibers in said array at said light receiving end wall will be reduced as it passes through said fibers in said array in order that said self-scanning photodiode array means can be smaller in length than said scintillator means.
2. The apparatus of claim 1 including
   said fiber optic array being of generally uniform thickness.
3. The apparatus of claim 1 including
   said light receiving end wall forming an angle with respect to one of said sidewalls of about 20 to 45 degrees.

* * * * *

UNITED STATES PATENT AND TRADEMARK OFFICE
CERTIFICATE OF CORRECTION

PATENT NO. : 4,946,238

DATED : August 7, 1990

INVENTOR(S) : DONALD SASHIN and ERNEST J. STERNGLASS

It is certified that error appears in the above-identified patent and that said Letters Patent is hereby corrected as shown below:

Col. 1, line 20, a period --.-- should be inserted after "environments".

Col. 1, line 26, "various" should be --Various--.

Col. 2, line 7, --the-- should be inserted after "by".

Col. 2, line 53, "couple" should be --coupler--.

Col. 3, line 18, "an" should be --and--.

Col. 3, line 68, "20 21" should be --20, 21--.

Col. 4, line 2, "20 21" should be --20, 21--.

Col. 5, line 32, "note" should be --noted--.

Col. 6, line 67, "123" should be --124--.

Signed and Sealed this

Twenty-first Day of April, 1992

Attest:

HARRY F. MANBECK, JR.

Attesting Officer   Commissioner of Patents and Trademarks